(12) United States Patent
Oh et al.

(10) Patent No.: US 8,519,108 B2
(45) Date of Patent: Aug. 27, 2013

(54) METHOD FOR PREPARING ANTIGEN EFFECTIVE FOR PREVENTING ANTHRAX INFECTION

(75) Inventors: Hee-Bok Oh, Seoul (KR); Bong-Su Kim, Seoul (KR); Gi-Eun Rhie, Seoul (KR); Jeong-Hoon Chun, Seoul (KR); Hun Kim, Suwon-si (KR); SinKoo Yeo, Yongin-si (KR); MahnHoon Park, Yongin-si (KR); Chong-Hwan Jonathan Chang, Yongin-si (KR); Mi Sun Ahn, Yongin-si (KR)

(73) Assignees: Korea Center For Disease Control and Prevention, Seoul (KR); Green Cross Corporation, Yongin-Si (KR)

( * ) Notice: Subject to any disclaimer, the term of this patent is extended or adjusted under 35 U.S.C. 154(b) by 441 days.

(21) Appl. No.: 12/812,176

(22) PCT Filed: Jan. 9, 2009

(86) PCT No.: PCT/KR2009/000134
§ 371 (c)(1),
(2), (4) Date: Oct. 4, 2010

(87) PCT Pub. No.: WO2009/088255
PCT Pub. Date: Jul. 16, 2009

(65) Prior Publication Data
US 2011/0015377 A1    Jan. 20, 2011

(30) Foreign Application Priority Data

Jan. 9, 2008  (KR) ........................ 10-2008-0002656

(51) Int. Cl.
*C07K 14/32*  (2006.01)
(52) U.S. Cl.
USPC ........ 530/417; 530/412; 530/414; 435/252.1; 435/252.5
(58) Field of Classification Search
None
See application file for complete search history.

(56) References Cited

U.S. PATENT DOCUMENTS

2004/0076638 A1   4/2004   Shiloach et al.
2004/0166120 A1   8/2004   Thomas et al.

FOREIGN PATENT DOCUMENTS

KR   10-2000-0031104 A   6/2000
WO   2006/110277 A1   10/2006

OTHER PUBLICATIONS

Rhie et al., "Expression and Secretion of the Protective Antigen of *Bacillus anthracis* in *Bacillus brevis*," FEMS Immunology and Medical Microbiology, 2005, vol. 45, pp. 331-339.

*Primary Examiner* — Padma V Baskar
(74) *Attorney, Agent, or Firm* — Sughrue Mion, PLLC

(57) ABSTRACT

The method of the present invention comprising successive column chromatography processes for the purification of an anthrax protective antigen can achieve an improved purity of the anthrax protective antigen product by effectively removing impurities (e.g., cellular residual proteins in the culture solution) without the loss of anthrax protective antigen. Therefore, the method of the present invention can be advantageously used for economically producing the anthrax protective antigen on a large scale.

11 Claims, 2 Drawing Sheets

FIG. 2

The peak of anthrax protective antigen

| | Name | RT | Area | Height | % Area |
|---|---|---|---|---|---|
| 1 | rPA(83kDa) | 7.487 | 1411587 | 43180 | 100.00 |

METHOD FOR PREPARING ANTIGEN EFFECTIVE FOR PREVENTING ANTHRAX INFECTION

FIELD OF THE INVENTION

The present invention relates to a method for preparing a highly pure agent for protecting against anthrax infection (anthrax protective antigen).

BACKGROUND OF THE INVENTION

Anthrax is a zoonotic disease transmissible between humans and animals, which is caused by Bacillus anthracis infection (Turnbull et al., WHO/EMC/ZDI, 3$^{rd}$ Ed. 1998). The pathogenesis of infection by B. anthracis is mainly related to the two exotoxins secreted thereby and the capsule, which are encoded on two plamids pXO1 and pXO2, respectively. The exotoxins of B. anthracis are composed of 3 different proteins; a protective antigen (PA), an edema factor (EF), and a lethal factor (LF), and these proteins are non-toxic when separated from each other. However, PA combines with either EF or LF to form an edema toxin or lethal toxin, with which protective antigens combine to facilitate the delivery of EF and LF into the cells. Further, PA is used for producing an anthrax vaccine for diagnosis or prevention because it is capable of inducing a protective antibody-response against B. anthracis infection. Accordingly, there have been numerous attempts to develop an effective method for producing PA on a large scale.

There have been reported methods for preparing such agents for preventing anthrax infection by combinant technologies using bacteria such as B. anthracis (Farchaus J W et al., Appl. Environ. Microbiol., 64, 982-991, 1998), B. subtilis (Baillie L et al., J. Appl. Microbiol., 84, 741-746, 1998) and E. coli (Laird M W et al., Protein Expr. Purif., 38, 145-152, 2004), and the usefulness of the anthrax protective antigens produced by the above methods has been described. Such recombinant anthrax protective antigens are generally purified by chromatography, and there have been many reports describing methods for purifying recombinant anthrax antigens by column chromatography. For example, Farchaus J W et al. (Appl. Environ. Microbiol., 64, 982-991, 1998) discloses a method of purifying anthrax protective antigen by ultrafiltration, ion exchange chromatography and hydrophobic chromatography; Gupta P et al. (Protein Expr. Purif., 16, 369-376, 1999), a method of purifying anthrax protective antigen by nickel affinity chromatography; and Laird M W et al. (Protein Expr. Purif., 38, 145-152, 2004), a method of purifying anthrax protective antigen by ion exchange chromatography and hydroxyapatite chromatography.

However, the above methods are uneconomical due to their complicated purification steps and the required use of expensive resins.

Therefore, there is a need for an improved method for preparing in a large scale a highly pure antigen for preventing anthrax infection, which is superior to the conventional methods in terms of maintaining the agent's immunogenicity, stability and safety.

SUMMARY OF THE INVENTION

Accordingly, it is an object of the present invention to provide an efficient, high yield method for preparing a highly pure anthrax protective antigen.

In accordance with one aspect of the present invention, there is provided a method for preparing the anthrax protective antigen, comprising the steps of 1) adjusting the conductivity of a solution containing an anthrax protective antigen in the range of 13 to 15 mS/cm, and subjecting the solution to ion exchange chromatography to obtain an eluted fraction containing the anthrax protective antigen; 2) adjusting the conductivity of the eluted fraction obtained in step 1) in the range of 1 to 5 mS/cm, and subjecting the resulting solution to ion exchange chromatography to obtain an eluted fraction containing the anthrax protective antigen; 3) adjusting the conductivity of the eluted fraction obtained in step 2) in the range of 170 to 175 mS/cm, and subjecting the resulting solution to hydrophobic column chromatography to obtain an eluted fraction containing the anthrax protective antigen; 4) exchanging the solvent in the eluted fraction obtained in step 3) by ultrafiltration and dialysis to obtain an antigen solution having a conductivity in the range of 5 to 10 mS/cm; and 5) subjecting the antigen solution obtained in step 4) to hydroxyapatite chromatography to obtain the anthrax protective antigen.

BRIEF DESCRIPTION OF THE DRAWINGS

The above and other objects and features of the present invention will become apparent from the following description of the invention, when taken in conjunction with the accompanying drawings, which respectively show:

FIG. 2: the result of gel permeation chromatography for confirming the purity of the anthrax protective antigen prepared by the inventive method, which shows the anthrax protective antigen peak at 7-9 min of retention time.

DETAILED DESCRIPTION OF THE INVENTION

Figure 1:
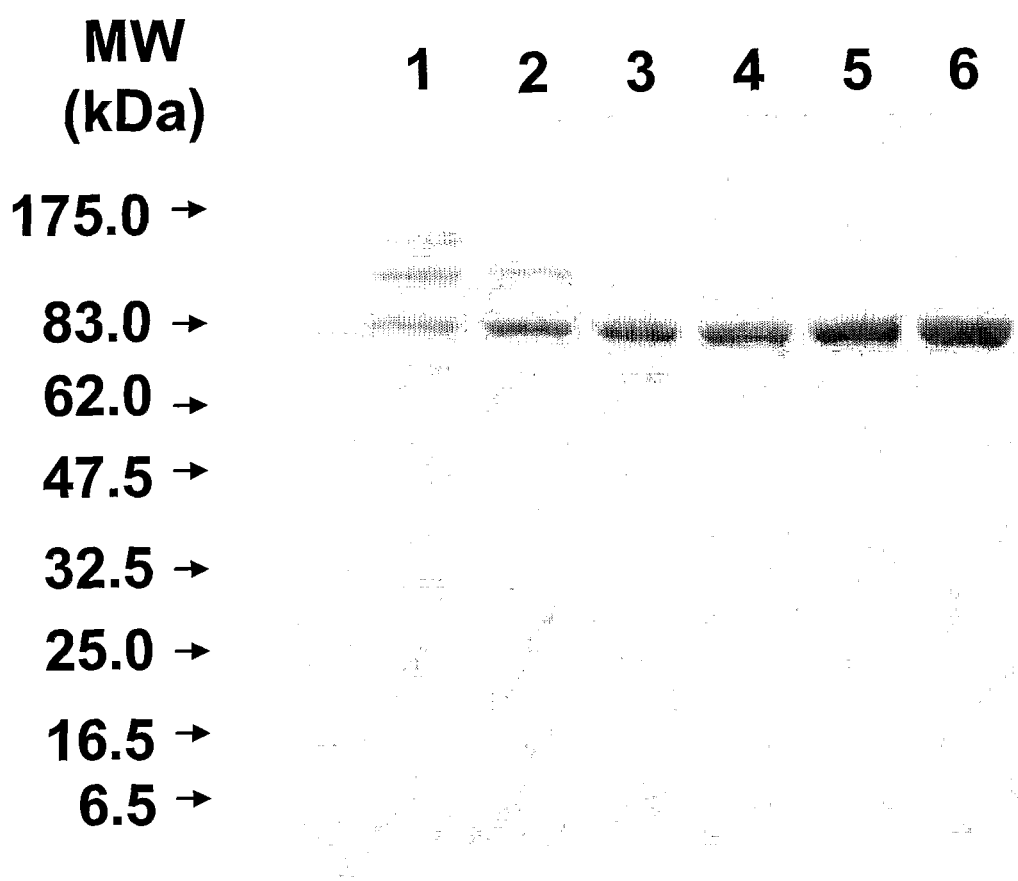
FIG. 1: the result of 4-20% gradient SDS-PAGE for determining the purity of the anthrax protective antigen prepared by the inventive method, Lane 1: molecular weight marker, Lane 2: the culture solution of Bacillus brevis used in Example 1, Lane 3: the eluted fraction obtained from the primary ion exchange chromatography in Step 1 of Example 1, Lane 4: the eluted fraction obtained from the secondary ion exchange chromatography in Step 2 of Example 1, Lane 5: the eluted fraction obtained from the hydrophobic chromatography in Step 3 of Example 1, Lane 6: the antigen solution obtained from the ultrafiltration and the dialysis processes in Step 4 of Example 1, Lane 7: the purified solution obtained from the hydroxyapatite chromatography in Step 5 of Example 1.

The method of the present invention comprising successive column chromatography processes can achieve the purification of an anthrax protective antigen to a high purity by effectively removing impurities (e.g., cellular residual proteins in the culture solution) without the loss of the anthrax protective antigen.

In step 1) of the inventive method, the eluted fraction containing the anthrax protective antigen may be obtained by adjusting the conductivity of the solution containing anthrax protective antigen in the range of 13 to 15 mS/cm; and subjecting the adjusted solution to an equilibrated column chromatography to remove the residual proteins.

The solution containing anthrax protective antigen may be a culture solution of cells producing recombinant anthrax protective antigen or any one of the known solutions containing anthrax protective antigen, which includes a culture solution of Bacillus brevis producing recombinant anthrax protective antigen, i.e., 47-5Q pNU212-mPA cells (Rhie G E et al., *FEMS Immunol Med Microbiol.*, 45, 331-339, 2005). Preferably, such a culture solution may be subjected to filter-sterilization using a 0.22 μm filter before to application to the column.

The ion exchange chromatography in step 1) may be performed by adjusting the conductivity of the solution containing the anthrax protective antigen in the range of 13 to 15 mS/cm, and introducing the solution to the ion exchange column. The conductivity of the solution may be adjusted using an electrolyte such as NaCl, LiCl, and $CH_3COONa$, preferably NaCl, and the column may be equilibrated using the same electrolyte. The column may be filled with any one of the known ion exchange resins, which include but not limited, to Q-Sepharose FF (quaternary ammonium), Q-Sepharose XL (quaternary amino), Macro-Prep High Q (quaternary ammonium), Macro-Prep 25 Q (quaternary ammonium), and SuperQ-650M (quaternary ammonium), preferably Q-Sepharose FF. The eluent used in the ion exchange chromatography of step 1) may be bis-tris propane, triethanolamine or tris. When the solution containing anthrax protective antigen is applied to the ion exchange column, the cellular residual proteins are absorbed on the column while the anthrax protective antigen passes through.

In step 2) of the inventive method, the eluted fraction containing the anthrax protective antigen may be obtained by adding distilled water to the eluted fraction obtained in step 1) so as to adjust the conductivity of the fraction in the range of 5 or less mS/cm, preferably 1 to 5 mS/cm; and subjecting the adjusted solution to chromatography using an equilibrated ion exchange column having the same conductivity to remove residual proteins.

The column may be filled with any one of the known ion exchange resins, which include but not limited to, Q-Sepharose FF (quaternary ammonium), Q-Sepharose XL (quaternary amino), Macro-Prep High Q (quaternary ammonium), Macro-Prep 25 Q (quaternary ammonium), and SuperQ-650M (quaternary ammonium), preferably Q-Sepharose FF, and the eluent used in the ion exchange chromatography may be bis-tris propane, triethanolamine or tris. In order to remove the residual proteins without the loss of the anthrax protective antigen, the ion exchange chromatography may be performed while maintaining the NaCl concentration in the eluent at 100 mM to obtain an eluted fraction containing the anthrax protective antigen.

In step 3) of the inventive method, the eluted fraction containing anthrax protective antigen may be obtained by adjusting the conductivity of the eluted fraction obtained in step 2) in the range of 170 or more mS/cm, preferably 170 to 175 mS/cm; and subjecting the adjusted solution to hydrophobic chromatography.

The conductivity of the eluted fraction may be adjusted using an electrolyte such as $(NH_4)_2SO_4$, $K_2SO_4$, $Na_2HPO_4$, and NaCl, preferably $(NH_4)_2SO_4$, and the column may be equilibrated using the same electrolyte so as to have the same conductivity as the adjusted solution. The column may be filled with any one of the known ion exchange resins, which include but not limited to, Butyl-S Sepharose 6 FF (butyl sulfate), Phenyl Sepharose 6 FF (phenyl), Phenyl-650 (phenyl), and Butyl-650 (butyl), preferably Butyl-S Sepharose 6 FF. The eluent used in the hydrophobic chromatography may be $NH_4(C_2H_3O_2)$, $NaH_2PO_4$, NaAc, or tris, and in order to remove the residual proteins without the loss of anthrax protective antigen, the chromatography may be performed using a linear gradient method by lowering the concentration of the eluent from 1.4 M to 0 M, to obtain an eluted fraction containing anthrax protective antigen.

In step 4) of the method of the present invention, the ultrafiltration process may be conducted using a 5 to 50 kDa UF (ultrafiltration) membrane, preferably a about 30 kDa UF membrane, and the ultrafiltration and dialysis processes may be carried out in one step after replacing the solvent of the eluted fraction obtained in step 3) with PBS or sodium phosphate, to obtain an antigen solution having a conductivity of 10 or less mS/cm, preferably 5 to 10 mS/cm.

In step 5) of the method of the present invention, the anthrax protective antigen may be obtained by subjecting the antigen solution obtained in step 4) to hydroxyapatite chromatography. The column used in the hydroxyapatite chromatography process may be equilibrated with a buffer containing the same electrolyte as employed in step 4), and may be filled with any one of the known hydroxyapatite resins, which include but not limited to, hydroxyapatite type I resin (calcium phosphate) and hydroxyapatite type II resin (calcium phosphate), preferably hydroxyapatite type II resin. The eluent employed in the hydroxyapatite chromatography process may be PBS or sodium phosphate, and the chromatography process may be conducted by a linear gradient method by increasing the concentration of the eluent from 5 mM to 300 mM so as to obtain the highly pure anthrax protective antigen.

The following Examples are intended to further illustrate the present invention without limiting its scope.

Example 1

Purification of Anthrax Protective Antigen Using Successive Column Chromatography Processes Step 1) Primary Ion Exchange Chromatography In order to remove cellular impurities such as pigment materials and residual proteins in a culture solution, a preliminary ion exchange chromatography process was performed as follows:

200/16 GPG column (Pharmacia) was filled with 5024 Ml of Q-Sepharose FF (Pharmacia), and connected to an ion exchange chromatography system (Pharmacia). The resin was washed by passing 3-5 times the resin volume of 1 N NaOH through the column at a flow rate of 100 cm/hr, and activated by passing 3-5 times the resin volume of 1 N NaCl through the column at a flow rate of 100 cm/hr. Then, the column was washed and equilibrated by passing 3-5 times the resin volume of 50 mM tris-HCl buffer (pH 7.5, 100 mM NaCl) therethrough at a flow rate of 100 cm/hr to remove residual salts.

Meanwhile, *Bacillus brevis* 47-5Q pNU212-mPA strain producing an anthrax protective antigen (The Korea Centers for Disease Control and Prevention (KCDC), expanding National Institute of Health, Center for Infectious Diseases, Division of High-risk Pathogen Research) was cultured at a condition of 30° C. and 220 rpm, and 20 L of the culture solution was filter-sterilized. The conductivity of the sterilized culture solution was adjusted to 14 mS/cm with 3 M NaCl, and passed through the above equilibrated column at a flow rate of 100 cm/hr. The column was eluted with 24 L of 50 mM tris-HCl buffer (pH 7.5, 100 mM NaCl) to obtain an eluted fraction containing the anthrax protective antigen.

Step 2) Secondary Ion Exchange Chromatography

In order to remove the residual impurities in the eluted fraction obtained in Step 1, the secondary ion exchange chromatography process was performed as follows:

The ion exchange chromatography system is prepared by repeating the process of Step 1 except for using 300/15 amicon module column (Millipore) filled with 10,600 Ml of the same resin as used in Step 1.

The conductivity of 24 L of the eluted fraction obtained in Step 1 was adjusted to 5 mS/cm with 75.6 L of triply distilled water, and the resulting solution was passed through the equilibrated column at a flow rate of 100 cm/hr. The column was eluted with 12 L of 50 mM tris-HCl buffer (pH 7.5, 100 mM NaCl) to obtain an eluted fraction containing the anthrax protective antigen.

Step 3) Hydrophobic Chromatography

In order to remove the residual impurities in the eluted fraction obtained in Step 2, the hydrophobic chromatography process was performed as follows:

5/26 XK column (Pharmacia) was filled with 510 Ml of Butyl-S Sepharose 6 FF (Pharmacia), and connected to a hydrophobic chromatography system (Pharmacia). The column was washed by passing 3-5 times the resin volume of 1 N NaOH therethrough at a flow rate of 150 cm/hr; activated by passing 3-5 times the resin volume of 50 mM tris-HCl buffer (pH 7.5) therethrough at a flow rate of 150 cm/hr; and washed and equilibrated by passing 3-5 times the resin volume of 50 mM tris-HCl buffer (pH 7.5, 1.4 M $(NH_4)_2SO_4$) therethrough at a flow rate of 100 cm/hr.

Meanwhile, the conductivity of 7.1 L of the eluted fraction obtained in step 2 was adjusted to 170 mS/cm with 8.2 L of 3 M $(NH_4)_2SO_4$, and the resulting solution was passed through the equilibrated column at a flow rate of 150 cm/hr. The column was eluted by a linear gradient decreasing from 1.4 M to 0 M using 1800 Ml of 50 mM tris-HCl buffer (pH 7.5) to obtain an eluted fraction containing the anthrax protective antigen.

Step 4) Ultrafiltration and Dialysis

For solvent-replacement and reduced conductivity, the ultrafiltration and dialysis processes were performed as follows:

The eluted fraction obtained in Step 3 was filtered using a UF concentrator (VIVASCIENCE) equipped with a 30 kDa UF module at an inlet pressure of 2 bar, together with replacing with the solvent therein into 5 mM sodium phosphate (pH 7.5), to obtain an antigen solution having a conductivity of 5 mS/cm.

Step 5) Hydroxyapatite Chromatography

In order to remove the residual impurities in the antigen solution obtained in Step 4 without the loss of the anthrax protective antigen, the hydroxyapatite chromatography process was performed as follows:

5/27 XK column (Pharmacia) was filled with 530 Ml of Hydroxyapatite type II resin (BIO-RAD), and connected to a chromatography system (Pharmacia). The column was washed by passing 3-5 times the resin volume of 1 N NaOH therethrough at a flow rate of 200 cm/hr; activated by passing 3-5 times the resin volume of 300 mM sodium phosphate buffer (pH 7.5) therethrough at a flow rate of 200 cm/hr; and washed and equilibrated by passing 3-5 times the resin volume of 5 mM sodium phosphate buffer (pH 7.5) therethrough at a flow rate of 200 cm/hr.

400 Ml of the antigen solution obtained in Step 4 was passed through the equilibrated hydroxyapatite type II column at a flow rate of 200 cm/hr, followed by eluting the column by a linear gradient increasing from 5 mM to 300 mM using 1800 Ml of 5 mM sodium phosphate buffer (pH 7.5) to obtain an eluted fraction containing the anthrax protective antigen. After completion of the passage, the column was eluted with 900 Ml of 300 mM sodium phosphate buffer (pH 7.5) to obtain a purified solution containing the anthrax protective antigen.

Test Example 1

Determination of the Purity of Anthrax Protective Antigen Using SDS-PAGE 4-20% gradient SDS-PAGE was conducted using the culture solution of *Bacillus brevis* 47-5Q pNU212-mPA employed in Step 1, the eluted fractions obtained in Steps 1 to 3, the antigen solution obtained in Step 4 and the purified solution obtained in Step 5 of Example 1. The result is shown in FIG. 1.

In FIG. 1, lane 1 is a molecular weight marker; lane 2 is the culture solution of *Bacillus brevis* 47-5Q pNU212-mPA; lane 3 is the eluted fraction obtained from the primary ion exchange chromatography in Step 1 of Example 1; lane 4 is the eluted fraction obtained from the secondary ion exchange chromatography in Step 2 of Example 1; lane 5 is the eluted fraction obtained from the hydrophobic chromatography in Step 3 of Example 1; Lane 6 is the antigen solution obtained from the ultrafiltration and dialysis processes in Step 4 of Example 1; and lane 7 is the purified solution obtained from the hydroxyapatite chromatography in Step 5 of Example 1. As shown in FIG. 1, 83 kDa protein bands corresponding to the molecular weight of the anthrax protective antigen can be observed in all samples, which confirm the existence of the anthrax protective antigen. The band thickness increased stepwise from the sample of Step 1 to the sample of Step 5, which suggests that the purity of the anthrax protective antigen become higher as the steps of the inventive method were conducted.

Further, the purified solution obtained from the hydroxyapatite chromatography in Step 5 of Example 1 was subjected to GP-HPLC column chromatography (column: G2000SWXL-TOSOH, eluent: 1×PBS (pH7.5), flow rate: 1 mL/min, inlet volume: 20.40 μl). The result is shown in FIG. 2.

As shown in FIG. 2, no impurity peak was present, while the anthrax protective antigen peak was detected (100% purity), which confirms that it is possible to obtain highly pure anthrax protective antigen according to the method of the present invention.

Test Example 2

Enzyme Immunoassay for Analyzing the Yield of Anthrax Protective Antigen

In order to determine the yield of the anthrax protective antigen obtained by the method of the present invention, enzyme immuno assay with a AniGen Anthrax Ag ELISA Q kit (AniGen; Korea) was conducted using the culture solution of *Bacillus brevis* 47-5Q pNU212-mPA employed in Step 1, the eluted fractions obtained in Steps 1 to 3, the antigen solution obtained in Step 4 and the purified solution obtained in Step 5 of Example 1 according to manufacturer's instructions, as follows.

First, in a primary antibody (an anti-anthrax monoclonal antibody RPAn1 supplied by GREEN CROSS Co.)-coated 96 well plate, a negative control sample (containing bovine serum albumin (BSA) and 0.05 v/v % procline) was added to each of 3 wells as a negative control, a positive control sample (containing a diluted solution of purified anthrax antigen and 0.05 v/v % procline) was added to each of another 3 wells, and 50 μl of test samples 1 to 5 were each added to other wells (test sample 1—the culture solution of *Bacillus brevis* 47-5Q pNU212-mPA; test sample 2—the eluted fraction obtained from the primary ion exchange chromatography in Step 1 of Example 1; test sample 3—the eluted fraction obtained from the secondary ion exchange chromatography in Step 2 of Example 1; test sample 4—the eluted fraction obtained from the hydrophobic chromatography in Step 3 of Example 1; test sample 5—the antigen solution obtained from the ultrafiltration and dialysis processes in Step 4 of Example 1; and test sample 6—the purified solution obtained from the hydroxyapatite chromatography in Step 5 of Example 1). 50 µl of a conjugate solution (containing peroxidase/anti-anthrax monoclonal antibody (Anthrax-41-24-14; GREEN CROSS Co.) conjugate, BSA and 0.05 v/v % Kathon CG (Rohm & Hass) was added to each of the positive control and test wells, mixed well, and incubated at 37° C. for 30 min. The incubated wells were each washed 6 times with a washing solution (containing tris-saline buffer, polysorbate 20 and 0.05 v/v % procline), and the residual washing solution was completely removed. 100 µl of a mixture of TMB (tetramethyl benzidine) and 30% hydrogen peroxide (1:1) as a substrate buffer was added to each well, and incubated at room temperature for 10 min. After the reaction was stopped by adding 100 µl of 1.6 N sulfuric acid to each well, the absorbance of each well was measured at a operating wavelength of 450 nm with a reference wavelength of 620 nm within 30 min. A graph of absorbance vs. concentration is set up to plot each absorbance value versus each concentration value of standard solutions, and the amount and yield of the anthrax protective antigen in each of the negative and positive controls and the test samples were evaluated based on the above graph. The results are shown in Table 1.

TABLE 1

| Control and test sample | Amount of the anthrax protective antigen (g) | Yield (%) |
| --- | --- | --- |
| Negative control | Absorbance ≦0.1 | — |
| Positive control | Absorbance ≧1.5 | — |
| Test sample 1 | 3.5 | 100 |
| Test sample 2 | 2.5 | 71.8 |
| Test sample 3 | 1.9 | 53.4 |
| Test sample 4 | 1.6 | 45.8 |
| Test sample 5 | 1.6 | 44.6 |
| Test sample 6 | 1.33 | 38.1 |

As shown in Table 1, the anthrax protective antigen can be obtained by the method of present invention with a high yield of 38.1 or more %.

While the invention has been described with respect to the above specific embodiments, it should be recognized that various modifications and changes may be made to the invention by those skilled in the art which also fall within the scope of the invention as defined by the appended claims.

What is claimed is:

1. A method for preparing a purified anthrax protective antigen, comprising the steps of
   1) adjusting the conductivity of a solution containing the anthrax protective antigen in the range of 13 to 15 mS/cm by adding NaCl, LiCl or CH$_3$COONa to the solution, and subjecting the solution to ion exchange chromatography to obtain an eluted fraction containing the anthrax protective antigen, wherein the ion exchange chromatography employs an ion exchange resin selected from the group consisting of Q-Sepharose FF (quaternary ammonium), Q-Sepharose XL (quaternary amino), Macro-Prep High Q (quaternary ammonium), Macro-Prep 25 Q (quaternary ammonium), and Super Q-650M (quaternary ammonium);
   2) adjusting the conductivity of the eluted fraction obtained in step 1) in the range of 1 to 5 mS/cm, and subjecting the resulting solution to ion exchange chromatography to obtain an eluted fraction containing the anthrax protective antigen, wherein the ion exchange chromatography employs an ion exchange resin selected from the group consisting of Q-Sepharose FF (quaternary ammonium), Q-Sepharose XL (quaternary amino), Macro-Prep High Q (quaternary ammonium), Macro-Prep 25 Q (quaternary ammonium), and Super Q-650M (quaternary ammonium);
   3) adjusting the conductivity of the eluted fraction obtained in step 2) in the range of 170 to 175 mS/cm by adding $(NH_4)_2SO_4$, $K_2SO_4$, $Na_2HPO_4$ or NaCl to the fraction, and subjecting the resulting solution to hydrophobic column chromatography to obtain an eluted fraction containing the anthrax protective antigen;
   4) exchanging the solvent in the eluted fraction obtained in step 3) by ultrafiltration and dialysis to obtain an antigen solution having a conductivity in the range of 5 to 10 mS/cm; and
   5) subjecting the antigen solution obtained in step 4) to hydroxyapatite chromatography to obtain a purified anthrax protective antigen.

2. The method of claim 1, wherein the solution containing the anthrax protective antigen in step 1) is a culture solution of a cell producing a recombinant anthrax protective antigen.

3. The method of claim 2, wherein the cell is *Bacillus brevis*.

4. The method of claim 1, wherein in step 2), the conductivity of the eluted fraction obtained in step 1) is adjusted by diluting the fraction with distilled water.

5. The method of claim 1, wherein the ion exchange chromatography processes of step 1) and step 2) are conducted using an eluent selected from the group consisting of bis-tris propane, triethanolamine, and tris.

6. The method of claim 1, wherein the hydrophobic chromatography process of step 3) is conducted using a resin selected from the group consisting of Butyl-S Sepharose 6 FF (butyl sulfate), Phenyl Sepharose 6 FF (phenyl), Phenyl-650 (phenyl), and Butyl-650 (butyl).

7. The method of claim 1, wherein the hydrophobic chromatography process of step 3) is conducted using an eluent selected from the group consisting of $NH_4(C_2H_3O_2)$, $NaH_2PO_4$, NaAc, and tris.

8. The method of claim 1, wherein the ultrafiltration process of step 4) is conducted using a 5 to 50 kDa ultrafiltration membrane.

9. The method of claim 1, wherein in step 4), the solvent of the eluted fraction obtained in step 3) is replaced with phosphate buffered saline or sodium phosphate.

10. The method of claim 1, wherein the hydroxyapatite chromatography process of step 5) is conducted using a resin selected from the group consisting of hydroxyapatite type I resin (calcium phosphate) and hydroxyapatite type II resin (calcium phosphate).

11. The method of claim 1, wherein the hydroxyapatite chromatography process of step 5) is conducted using an eluent selected from the group consisting of phosphate buffered saline and sodium phosphate.

* * * * *